(12) United States Patent
Choi et al.

(10) Patent No.: US 9,439,937 B2
(45) Date of Patent: Sep. 13, 2016

(54) RAT-EYE BEAN EXTRACT IMPROVING BLOOD GLUCOSE CONTROL AND BIOACTIVITY AND METHOD OF PRODUCING THE SAME

(75) Inventors: Byeongcheol Choi, Busan (KR); Kyoungsuk Kim, Busan (KR); Baejin Ha, Busan (KR)

(73) Assignees: ByeongCheol Choi, Busan (KR); Kyoungsuk Kim, Busan (KR); Grandmother's Cheong Gug Jang of 50 Year's Tradition Co., Ltd., Busan (KR)

( * ) Notice: Subject to any disclaimer, the term of this patent is extended or adjusted under 35 U.S.C. 154(b) by 502 days.

(21) Appl. No.: 13/995,210

(22) PCT Filed: Jun. 18, 2012

(86) PCT No.: PCT/KR2012/004801
§ 371 (c)(1),
(2), (4) Date: Jun. 18, 2013

(87) PCT Pub. No.: WO2013/118948
PCT Pub. Date: Aug. 15, 2013

(65) Prior Publication Data
US 2014/0004211 A1 Jan. 2, 2014

(30) Foreign Application Priority Data
Feb. 8, 2012 (KR) ........................ 10-2012-0013004

(51) Int. Cl.
*A61K 36/48* (2006.01)
*A23L 1/30* (2006.01)
*A23L 2/38* (2006.01)

(52) U.S. Cl.
CPC .............. *A61K 36/48* (2013.01); *A23L 1/3002* (2013.01); *A23L 2/38* (2013.01)

(58) Field of Classification Search
None
See application file for complete search history.

(56) References Cited

FOREIGN PATENT DOCUMENTS

| KR | 10-2002-0084666 A | 11/2002 |
|----|-------------------|---------|
| KR | 10-2006-0016627 A | 2/2006 |
| KR | 10-0659015 B1 | 12/2006 |
| KR | 10-0778044 B1 | 11/2007 |
| KR | 10-2010-0115553 A | 10/2010 |
| KR | 10-2011-0053813 A | 5/2011 |

OTHER PUBLICATIONS

Lee et al. Abstract of KR 2006065250 A. Jun. 14, 2006.*

* cited by examiner

*Primary Examiner* — Amy L Clark
(74) *Attorney, Agent, or Firm* — Rabin & Berdo, P.C.

(57) ABSTRACT

Provided are a rat-eye bean extract improving blood glucose control and bioactivity, which is produced from rat-eye beans as health food so as to be able to improving storability, portability and potability, and a method of producing the same. The rat-eye bean extract is produced by putting rat-eye beans, which are cleanly washed without foreign materials and are soaked in water for five hours, and water into a steam pot at a volume ratio of 3:1 along with rice straw, fermenting water, which is boiled to steam the rat-eye beans in weak flames for five hours, in a hot-floored room for two to three days, putting the fermented water and a grapefruit juice into the steam pot at a weight ratio of 99:1, and heating a mixture of the fermented water and the grapefruit juice in a closed state at a temperature of 110 to 120° C. for four to five hours.

1 Claim, 6 Drawing Sheets

FIG. 11 ized to a block diagram of a method of producing a rat-eye bean extract provided in the present invention;
RAT-EYE BEAN EXTRACT IMPROVING BLOOD GLUCOSE CONTROL AND BIOACTIVITY AND METHOD OF PRODUCING THE SAME

TECHNICAL FIELD

The present invention relates, in general, to an extract made from a rat-eye bean (nomenclature: *Rhynchosia volubilis*) and a method of producing the same and, more particularly, to a rat-eye bean extract improving blood glucose control and bioactivity, which is produced from rat-eye beans as health food so as to be able to improving storability, portability, and potability, and a method of producing the same.

BACKGROUND ART

According to Compendium of Materia Medica (also known as Bencao Gangmu), a rat-eye bean is known to be better when a male bean, which is black, glossy, and small, is used as a medicine. It is known that, when the rat-eye bean is cultivated in the soil mixed with sulfur, its medicinal benefits get better. The rat-eye bean is warm, sweet, and nonpoisonous.

Further, according to Dongui Bogam, it is known that the rat-eye bean has good effect on a renal disease, lowers energy to inhibit all kinds of wind heat, counteracts all poisons, and makes blood circulation active. Particularly, the rat-eye bean counteracts all the poisons including a poison of mineral medicinal stuff, and activates the blood circulation.

As already known, the rat-eye bean has a common nature, and is differently processed according to a symptom. Particularly, since an extract obtained by boiling down water with the rat-eye bean shows a very cold nature, the extract has an effect on a symptom that runs a high temperature and feels heavy and painful in the chest, and counteracts the poisons of all the medicines.

However, despite these pharmacological effects, the extract obtained by boiling down water with the rat-eye bean has a problem in that it is difficult to easily make the extract at home so as to take the extract for a long period.

Meanwhile, various health foods using the rat-eye bean have been developed. A representative example is health food that is disclosed in Korean Patent No. 10-0777351 (Nov. 19, 2007), uses a germinated rat-eye bean extract as an effective component, and is intended to prevent or cure osteoporosis. Here, the rat-eye bean extract is concentrated and dried so as to be added to a variety of foodstuffs.

Another example is health food that is disclosed in Korean Patent No. 10-0778044 (Nov. 29, 2007), titled "Method of Producing Health Food Using Isoflavon Contained in Rat-Eye Bean as Effective Component and Health Food Produced Thereby." To produce the health food, *Cornus officinalis, Acanthopanax Sessiliflorum, Schisandra chinensis, angelica gigas, Rehmannia glutinosa, Artemisia capillaries*, leaf of *Camellia sinensis*, and *Glycyrrhiza glabra* are put into a mixture of chokong (bean pickled in vinegar) and gamdutang (water boiled with *Glycyrrhiza glabra* and rat-eye beans), and an obtained concentrate is fermented and dried.

In most products using the rat-eye bean, it is difficult to be produced into a powdered product containing components of the rat-eye bean, and to sufficiently exert functionality of the rat-eye bean only because components of various medicinal stuffs are taken along with the components of the rat-eye bean.

RELATED ART DOCUMENTS

[Patent Document 1] KR 100777351 B1 (Nov. 19, 2007)
[Patent Document 2] KR 100778044 B1 (Nov. 29, 2007)

DISCLOSURE

Technical Problem

As such, the inventor has studied and developed a rat-eye bean extract so as to be able to easily take effective components of a rat-eye bean. Accordingly, the present invention is intended to provide a rat-eye bean extract improving blood glucose control and bioactivity, which is produced from rat-eye beans as health food so as to be able to improving storability, portability, and potability, and a method of producing the same.

Technical Solution

According to an aspect of the present invention, there is provided a rat-eye bean extract, which is produced by putting rat-eye beans, which are cleanly washed without foreign materials and are soaked in water for five hours, and water into a steam pot at a volume ratio of 3:1 along with rice straw, fermenting water, which is boiled to steam the rat-eye beans in weak flames for five hours, in a hot-floored room for two to three days, putting the fermented water and a grapefruit juice into the steam pot at a weight ratio of 99:1, heating a mixture of the fermented water and the grapefruit juice in a closed state at a temperature of 110 to 120° C. for four to five hours, cooling the heated mixture, and packing the cooled mixture in units of 50 to 100 milliliters using a pouch machine.

Advantageous Effects

According to the present invention, the rat-eye bean extract improving blood glucose control and bioactivity can be stored for a long period by a cold-storage method, and be packed in a small unit to provide excellent portability.

Further, main components of the rat-eye bean can be easily taken. When the rat-eye bean extract is taken for a long period, it is expected to inhibit diabetes, raise immunity, improve blood circulation, and provide valuable aid in preventing and cure various diseases, as in the examples.

BEST MODE

A method of producing a rat-eye bean extract improving blood glucose control and bioactivity includes: a washing and soaking process of cleanly washing rat-eye beans without foreign materials and soaking the washed rat-eye beans in water for five hours; a steaming process of putting the washed and soaked rat-eye beans into a steam pot along with rice straw, pouring water by ⅓ times a volume of the rat-eye beans, and steaming the rat-eye beans in weak flames for five hours; a fermenting process of fermenting the boiled water separated from the rat-eye beans steamed in the steam pot in a hot-floored room for two to three days; a sterilizing process of putting the fermented water and a grapefruit juice into the steam pot at a weight ratio of 99:1 and heating a mixture of the fermented water and the grapefruit juice in a closed state at a temperature of 110 to 120° C. for four to five hours; a cooling process of fully cooling the heated mixture at room temperature; and a packing process of packing the cooled mixture at a small amount of 50 to 100 milliliters so as to be potable once using a pouch machine.

Mode for Invention

Hereinbelow, a rat-eye bean extract improving blood glucose control and bioactivity and a method of producing the same according to an exemplary embodiment of the present invention will be described in detail with reference to the accompanying drawings.

Figure 1:
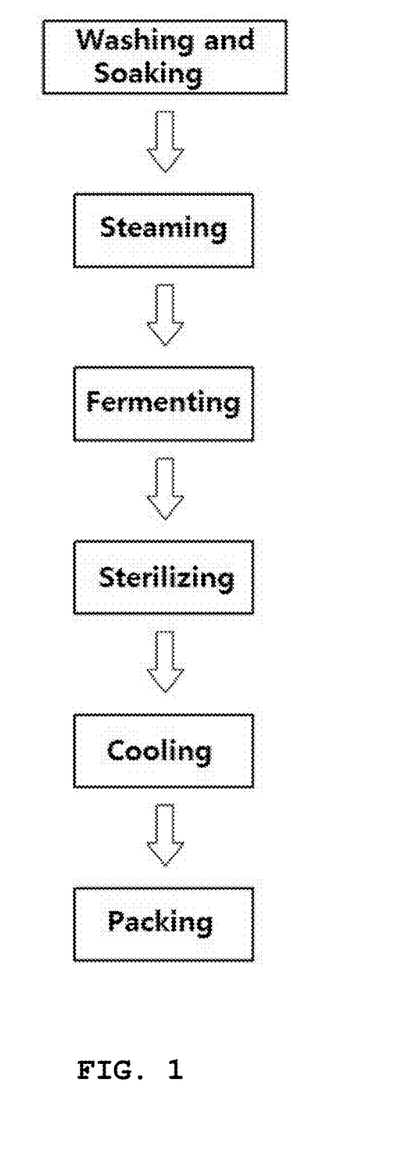
FIG. 1 is a block diagram of a method of producing a rat-eye bean extract provided in the present invention.

A rat-eye bean extract improving blood glucose control and bioactivity according to an exemplary embodiment of the present invention is produced by a producing method of FIG. 1 in the order of 1) washing and soaking, 2) steaming, 3) fermenting, 4) sterilizing, 5) cooling, and 6) packing.

For the producing method of the present invention, a rat-eye bean, rice straw, and a grapefruit are used.

The rat-eye bean is selected and used, which is cultivated at home and abroad and has a uniform size, a black color, and a glossy hull.

The rice straw is used which is obtained by threshing rice grown without blight, harmful insects, and insecticides and is neatly arranged by removing chips from the threshed rice. The rice straw abounds in bacilli, and the bacilli present in the rice straw serve as cultured bacteria fermenting the rat-eye bean.

The grapefruit is selected and used which has a smooth shell and no defects. The grapefruit is juicy and tastes sour, sweet, and a little bitter. Further, the grapefruit acts as a natural antiseptic and provides functionality of prolonging the period of circulation.

The rat-eye bean extract improving blood glucose control and bioactivity according to the exemplary embodiment of the present invention is produced by putting rat-eye beans, which are cleanly washed without foreign materials and are soaked in water for five hours, and water into a steam pot at a volume ratio of 3:1 along with rice straw, fermenting water, which is boiled to steam the rat-eye beans in weak flames for five hours, in a hot-floored room for two to three days, putting the fermented water and a grapefruit juice into the steam pot at a weight ratio of 99:1, and heating a mixture of the fermented water and the grapefruit juice in a closed state at a temperature of 110 to 120° C. for four to five hours.

Hereinafter, the producing method of the present invention will be described in greater detail.

1) Washing and Soaking

Rat-eye beans are cleanly washed without foreign materials, and are soaked in water for five hours. Here, a time required for soaking may be increased or decreased according to conditions of the rat-eye bean 2) Steaming The washed and soaked rat-eye beans are put into a steam pot, and water is poured by ⅓ times a volume of the rat-eye beans. Then, the rat-eye beans are steamed in weak flames for five hours. The weak flames refer to a degree to which weakest flames are formed on the basis of a gas range Here, a bundle of rice straw is put among the rat-eye beans put into the steam pot so that bacilli present in the rice straw can be transferred to the rat-eye beans.

For example, when 100 liters of the soaked rat-eye beans are mixed and steamed with 33 liters of water, about 20 liters of water can be obtained.

3) Fermenting

The water obtained by steaming the rat-eye beans as described above is put into a jug, and is fermented in a hot-floored room for two to three days.

Here, the hot-floored room is properly maintained under temperature condition of about 20 to 30° C., and thus the bacilli present in the rice straw are sufficiently proliferated.

4) Sterilizing

The rat-eye beans steamed in the steam pot as described above are separated from the boiled water.

Up to now, the boiled water is wasted, and the rat-eye beans are fermented into fermented soybeans or a soybean paste in a traditional method.

The present invention is designed to use the boiled water wasted up to now. The boiled water undergoing the fermentation and a grapefruit juice are put into a steam pot at a weight ratio of 99:1, and heated in a closed state at a temperature of 110 to 120° C. for four to five hours.

Here, the grapefruit juice and the boiled water are naturally mixed with each other, and are converted into an extract provided in the present invention. The grapefruit acts as a natural antiseptic, and functions to prolong the period of circulation.

The extract produced in the present invention is a liquid material that does not give out a bad smell and has a brown color.

5) Cooling

The extract produced as described above is completely cooled at room temperature.

6) Packing

The produced extract is transported to a pouch machine, and is automatically packed in a small size. The extract is packed at a small amount of 50 to 100 milliliters so as to be potable one, and is stored at a temperature of 5° C. or less. In this way, the extract can provide the period of circulation of one year.

The extract produced in this way is to process the water, which is for the most part wasted after being boiled to steam the rat-eye beans up to now, into health food again. When the rat-eye bean extract provided in the present invention is taken for a long period, it is expected to control blood glucose, raise physical immunity, improve blood circulation, and provide valuable aid in preventing and cure various diseases.

EXAMPLE 1

Figure 2:
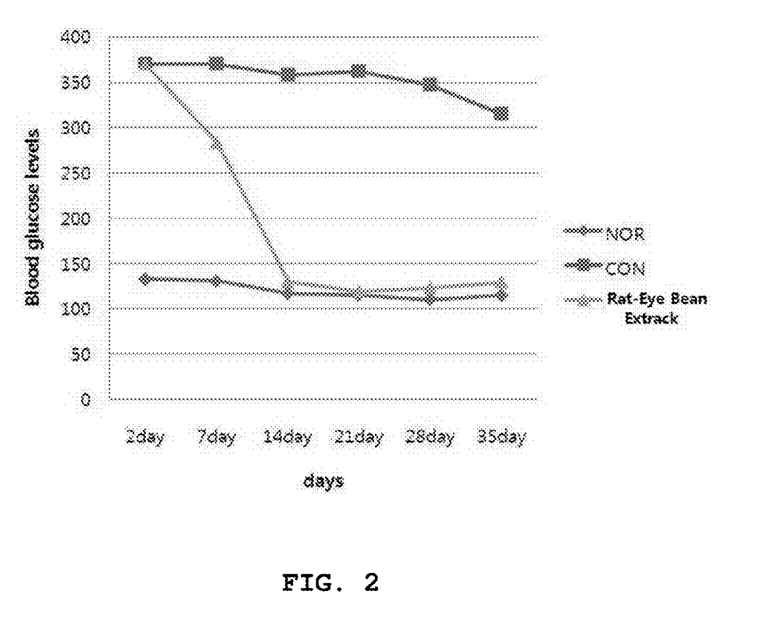
FIG. 2 is a graph showing an effect of a rat-eye bean extract produced in the present invention on blood glucose at diabetic mice induced with alloxan.

FIG. 2 is a graph showing an effect of a rat-eye bean extract produced in the present invention on blood glucose at diabetic mice induced with alloxan.

Group NOR is a normal group that does not suffer from diabetes. Group CON is a control group which suffers from diabetes. Group Rat-Eye Bean Extract is a group in which a rat-eye bean extract is administered to mice that suffer from diabetes.

Alloxan is known as a drug that damages pancreatic β-cell to cause type 1 diabetes. Mice induced with alloxan showed an increase in blood glucose three times or more compared to the normal group. In contrast, as a result of administering the rat-eye bean extract, the mice showed that the blood glucose was significantly reduced compared to the control group, and a recovery to the normal group.

EXAMPLE 2

Figure 3:
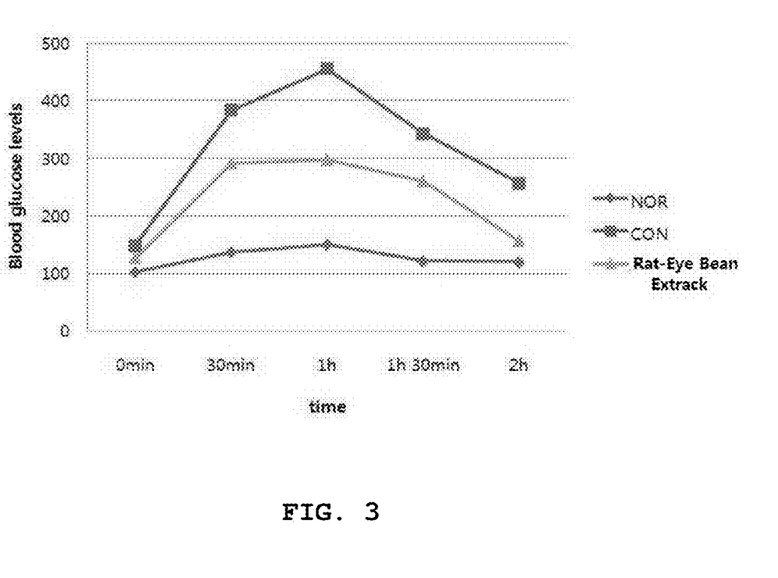
FIG. 3 is a graph showing an effect of a rat-eye bean extract produced in the present invention on glucose tolerance at diabetic mice induced with alloxan.

FIG. 3 is a graph showing an effect of a rat-eye bean extract produced in the present invention on glucose tolerance at diabetic mice induced with alloxan.

Group NOR is a normal group that does not suffer from diabetes. Group CON is a control group which suffers from diabetes. Group Rat-Eye Bean Extract is a group in which a rat-eye bean extract is administered to mice that suffer from diabetes.

2 g/kg of glucose was orally taken in a 12-hour fasting state. Then, a glucose level of blood was measured at intervals of 30 minutes for two hours so as to show a temporal variation in the glucose level. In normal, the glucose level was raised just after intake, but completely returned to normal after two hours. However, in the control group which suffered from diabetes, a high level was continuously maintained, and thus it took three hours or more to return to the level before intake. In the graph of FIG. 2, the control group shows the blood glucose level of 250 or more after two hours, but the group in which a rat-eye bean extract was administered nearly returned to normal.

EXAMPLE 3

Figure 4:
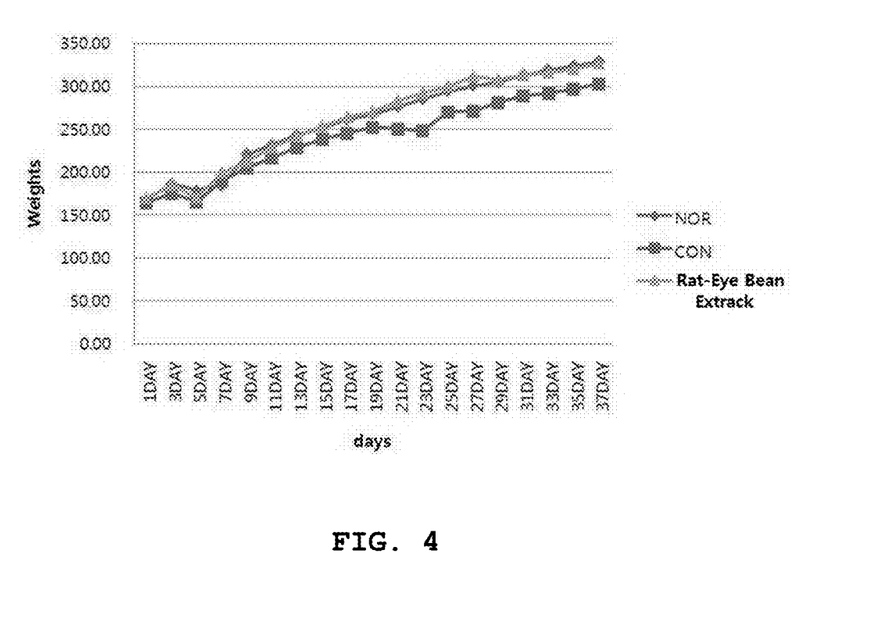
FIG. 4 is a graph showing an effect of a rat-eye bean extract produced in the present invention on weight at diabetic mice induced with alloxan.

FIG. 4 is a graph showing an effect of a rat-eye bean extract produced in the present invention on weight at diabetic mice induced with alloxan.

Group NOR is a normal group that does not suffer from diabetes. Group CON is a control group which suffers from diabetes. Group Rat-Eye Bean Extract is a group in which a rat-eye bean extract is administered to mice that suffer from diabetes.

As a daily dietary intake of a diabetic group was shown to be significantly high compared to a nondiabetic group, a polyphagia symptom resulting from diabetes was checked. It was reported that the reason the dietary intake of a diabetic mouse was higher than a normal mouse was caused by a decrease in the effect of a leptin receptor on a mouse short of insulin, and the dietary intake was reduced when insulin was supplemented.

In the present test, the dietary intake was significantly reduced by supply of the rat-eye bean extract, and returned to that similar to the normal group. This is shown in Table 1 below.

TABLE 1

| Amount of meal (g) | One week | Two weeks | Three weeks | Four weeks | Five weeks |
|---|---|---|---|---|---|
| NOR | 14.74 | 18.54 | 16.03 | 16.49 | 17.46 |
| CON | 19.20 | 23.97 | 22.98 | 22.01 | 22.13 |
| Rat-Eye Bean Extract | 17.62 | 20.93 | 20.52 | 19.63 | 18.93 |

Further, a change in weight can be an index of the diabetes. The alloxan-induced diabetic mouse was sharply reduced in growth, and a reduction in weight took place. As a result of administering the rat-eye bean extract, the sharp weight reduction during suffering from the diabetes was suppressed.

EXAMPLE 4

Figure 5:
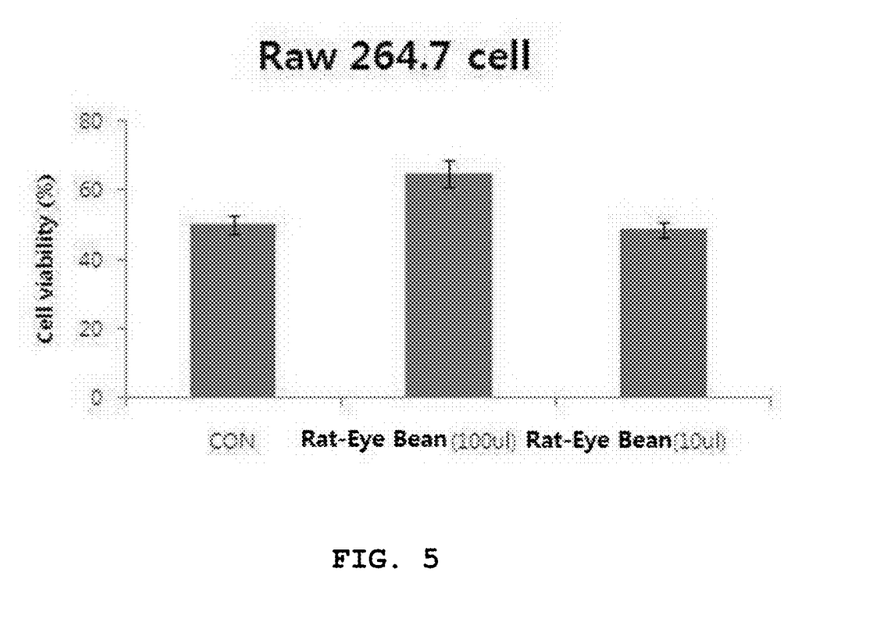
FIG. 5 is a graph showing a cytotoxicity effect of a rat-eye bean extract produced in the present invention on immunocytes, Raw 264.7 cells, from which inflammation is caused by lipopolysaccharide (LPS)

FIG. 5 is a graph showing a cytotoxicity effect of a rat-eye bean extract produced in the present invention on immunocytes, Raw 264.7 cells, from which inflammation is caused by lipopolysaccharide (LPS).

CON: It was checked that inflammation was killed by 50% from immunocytes, Raw 264.7 cells, from which inflammation is caused by LPS.

Rat-Eye Bean (100 ul): As a result of processing 100 ul of rat-eye bean extract at the immunocytes, Raw 264.7 cells, from which inflammation is caused by LPS, a cytotoxicity effect was shown by 64%.

Rat-Eye Bean (10 ul): As a result of processing 10 ul of rat-eye bean extract at the immunocytes, Raw 264.7 cells, from which inflammation is caused by LPS, the cytotoxicity effect was shown by 47%.

As described above, as a result of checking the cytotoxicity effect of the rat-eye bean extract on the immunocytes, Raw 264.7 cells, from which inflammation is caused by LPS, it was checked that a cell survival rate was increased at a concentration of 100 ul compared to the control group (Group CON). Thus, it was found that the rat-eye bean extract had the cytotoxicity effect.

EXAMPLE 5

Figure 6:
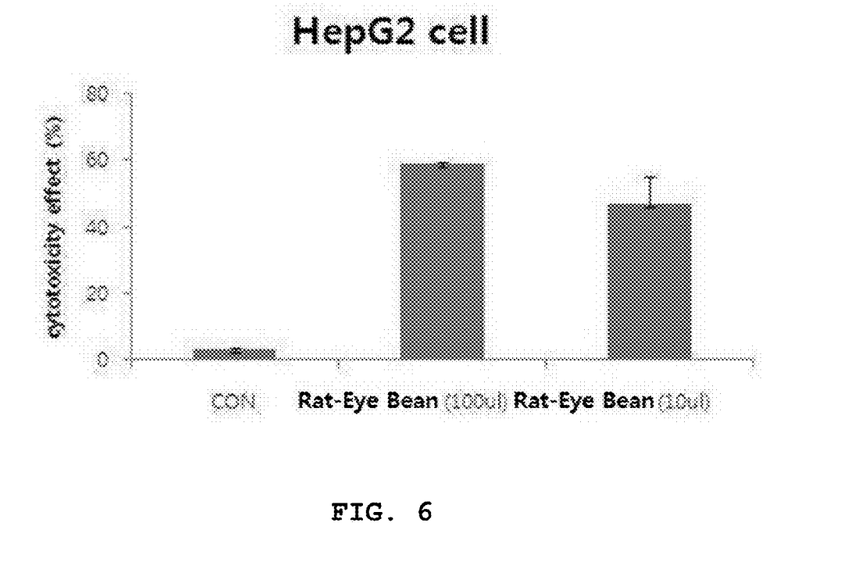
FIG. 6 is a graph showing an anticancer effect of a rat-eye bean extract produced in the present invention on hepatoma cells, HepG2 cells.

FIG. 6 is a graph showing an anticancer effect of a rat-eye bean extract produced in the present invention on hepatoma cells, HepG2 cells.

CON: Group in which a rat-eye bean extract was not processed for hepatoma cells, HepG2 cells.

Rat-Eye Bean (100 ul): 64% of anticancer effect was checked from a group in which 100 ul of rat-eye bean extract was processed for the hepatoma cells, HepG2 cells.

Rat-Eye Bean (10 ul): 48% of anticancer effect was checked from a group in which 10 ul of rat-eye bean extract was processed for the hepatoma cells, HepG2 cells.

As a result of checking anticancer activity of the rat-eye bean extract from the hepatoma cells, HepG2 cells, the anticancer activity was concentration-dependently increased by suppressing a survival rate of the hepatoma cells compared to the control group. Thus, it was checked that the rat-eye bean extract had the anticancer effect.

EXAMPLE 6

Figure 7:
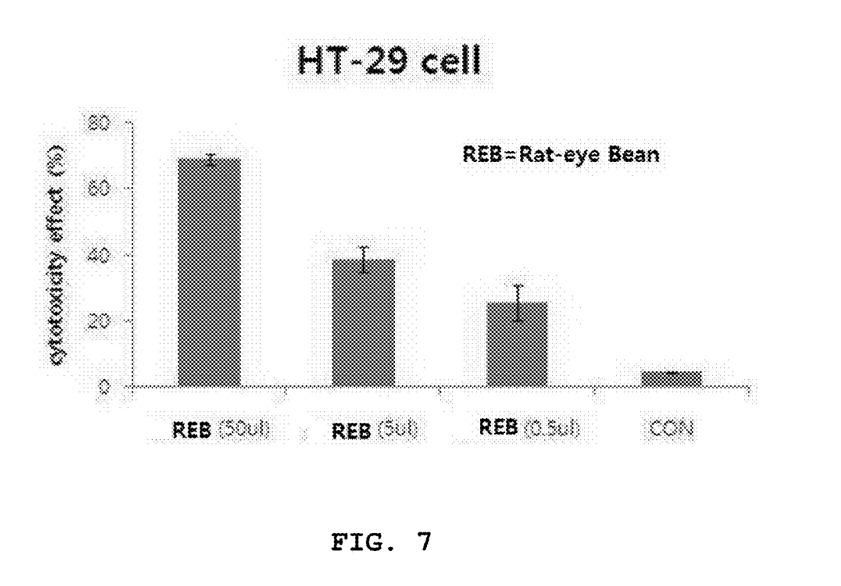
FIG. 7 is a graph showing an anticancer effect of a rat-eye bean extract produced in the present invention on colorectal cancer cells, HT-29 cells.

FIG. 7 is a graph showing an anticancer effect of a rat-eye bean extract produced in the present invention on colorectal cancer cells, HT-29 cells.

CON: Group in which a rat-eye bean extract was not processed for colorectal cancer cells, HT-29 cells.

Rat-Eye Bean (50 ul): 70% of anticancer effect was checked from a group in which 50 ul of rat-eye bean extract was processed for the colorectal cancer cells, HT-29 cells.

Rat-Eye Bean (5 ul): 38% of anticancer effect was checked from a group in which 50 ul of rat-eye bean extract was processed for the colorectal cancer cells, HT-29 cells.

Rat-Eye Bean (0.5 ul): 25% of anticancer effect was checked from a group in which 50 ul of rat-eye bean extract was processed for the colorectal cancer cells, HT-29 cells.

As a result of checking anticancer activity of the rat-eye bean extract from the colorectal cancer cells, HT-29 cells, the anticancer activity was concentration-dependently increased by suppressing a survival rate of the colorectal cancer cells compared to the control group. Thus, it was checked that the rat-eye bean extract had the anticancer effect.

EXAMPLE 7

Figure 8:
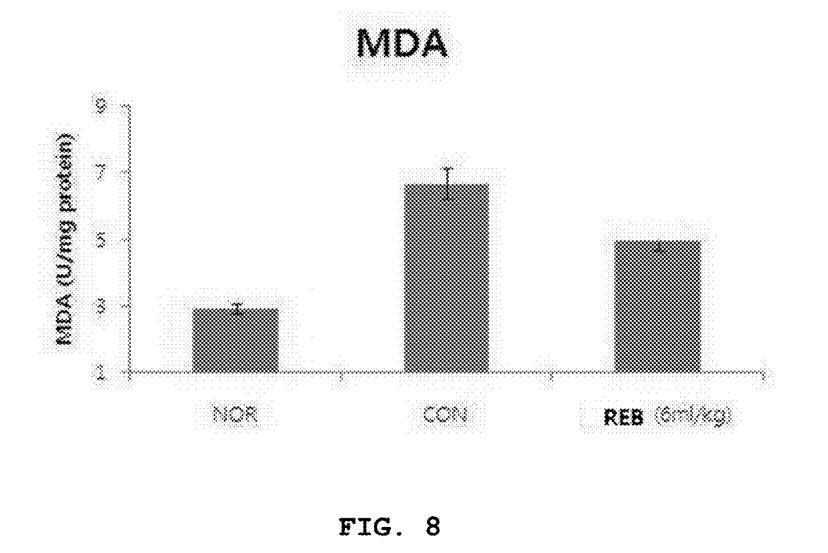
FIG. 8 is a graph showing an effect of a rat-eye bean extract produced in the present invention on a content of malondialdehyde (MDA) at white mice from which inflammation is caused by LPS.

FIG. 8 is a graph showing an effect of a rat-eye bean extract produced in the present invention on a content of malondialdehyde (MDA) at white mice from which inflammation is caused by LPS.

As a result of checking activity of an MDA enzyme that is a final product of lipid peroxidation at white mice from which inflammation is caused by LPS, it was checked that a control group was increased in MDA content by LPS compared to a normal group. It was checked that a group that took a rat-eye bean extract was rapidly recovered to the normal group compared to the control group. This, an effect of the rat-eye bean extract on inhibition of the lipid peroxidation was checked.

When MDA was excessively produced in a body by the lipid peroxidation, this was responsible for various adult diseases and aging.

EXAMPLE 8

Figure 9:
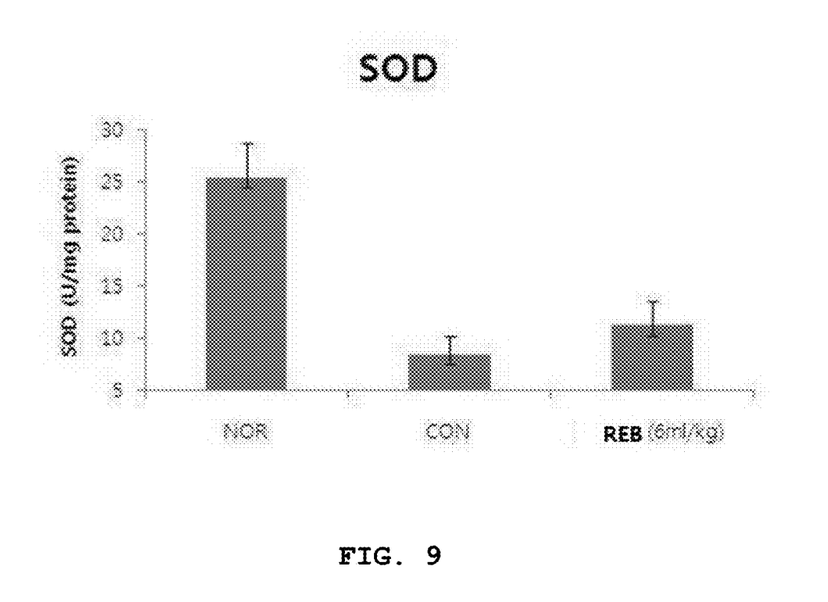
FIG. 9 is a graph showing an effect of a rat-eye bean extract produced in the present invention on a content of superoxide dismutase (SOD) at white mice from which inflammation is caused by LPS.

FIG. 9 is a graph showing an effect of a rat-eye bean extract produced in the present invention on a content of superoxide dismutase (SOD) at white mice from which inflammation is caused by LPS.

As a result of checking activity of a SOD enzyme which was a first step of antioxidase activity at white mice from which inflammation is caused by LPS, it was checked that a control group was reduced in SOD content by LPS compared to a normal group. It was checked that a group that took a rat-eye bean extract was rapidly recovered to the normal group compared to the control group. This, an effect of the rat-eye bean extract on the activity of the SOD enzyme was checked.

SOD: The SOD, antioxidase, converting active oxygen $O_2$ into $H_2O_2$ was present in a body. When balance in the body was destroyed, the activity of the SOD, antioxidase, was reduced. This was responsible for various adult diseases and aging.

EXAMPLE 9

Figure 10:
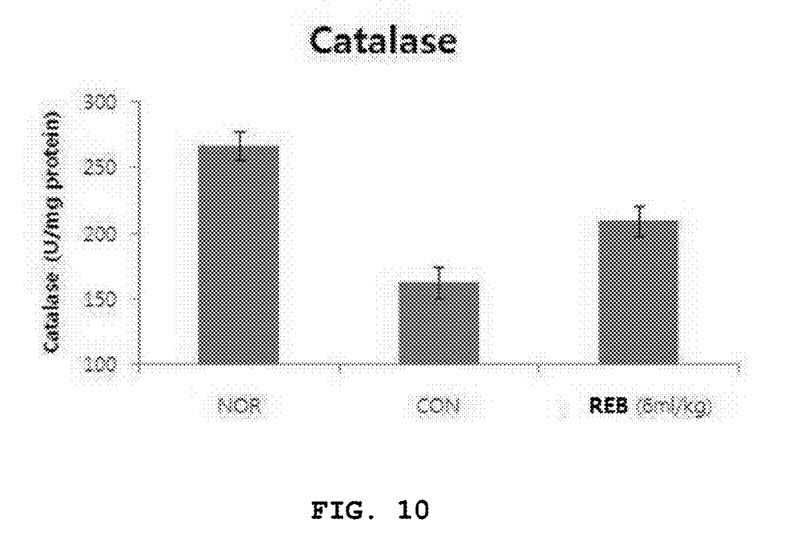
FIG. 10 is a graph showing an effect of a rat-eye bean extract produced in the present invention on a content of catalase at white mice from which inflammation is caused by LPS.

FIG. 10 is a graph showing an effect of a rat-eye bean extract produced in the present invention on a content of catalase at white mice from which inflammation is caused by LPS.

As a result of checking activity of a catalase enzyme which was a first step of antioxidase activity at white mice from which inflammation is caused by LPS, it was checked that a control group was reduced in catalase content by LPS compared to a normal group. It was checked that a group that took a rat-eye bean extract was rapidly recovered to the normal group compared to the control group. This, an effect of the rat-eye bean extract on the activity of the catalase enzyme was checked.

Catalase: The catalase, antioxidase, converting hydrogen peroxide ($H_2O_2$) into oxygen ($O_2$) and water ($H_2O$) was present in a body. When balance in the body was destroyed, the activity of the catalase, antioxidase, was reduced. This was responsible for various adult diseases and aging.

EXAMPLE 10

Figure 11:
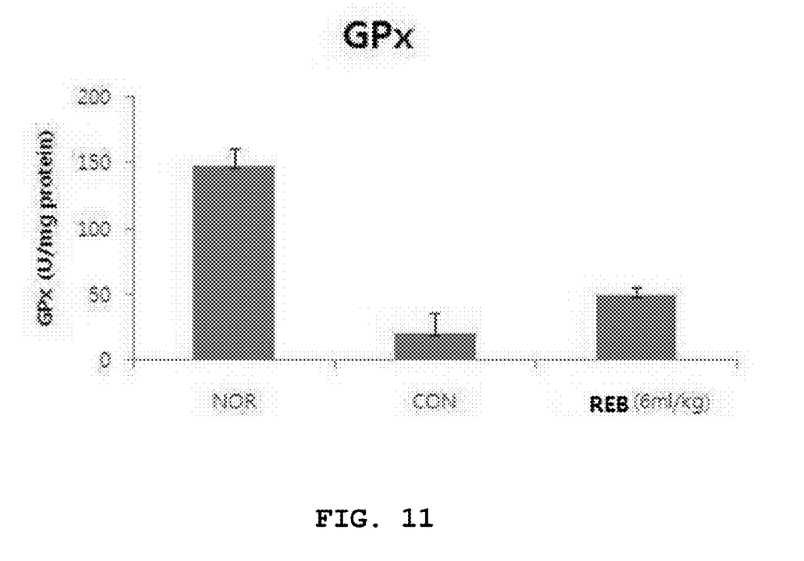
FIG. 11 is a graph showing an effect of a rat-eye bean extract produced in the present invention on a content of glutathione peroxidase (GPx) at white mice from which inflammation is caused by LPS.

FIG. 11 is a graph showing an effect of a rat-eye bean extract produced in the present invention on a content of glutathione peroxidase (GPx) at white mice from which inflammation is caused by LPS.

As a result of checking activity of a GPx enzyme which was a first step of antioxidase activity at white mice from which inflammation is caused by LPS, it was checked that a control group was reduced in GPx content by LPS compared to a normal group. It was checked that a group that took a rat-eye bean extract was rapidly recovered to the normal group compared to the control group. This, an effect of the rat-eye bean extract on the activity of the GPx enzyme was checked.

GPx: The GPx, antioxidase, converting hydrogen peroxide ($H_2O_2$) into oxygen ($O_2$) was present in a body. When balance in the body was destroyed, the activity of the GPx, antioxidase, was reduced. This was responsible for various adult diseases and aging.

Although the embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of producing a portable, rat-eye bean extract for improving and controlling blood glucose comprising:
   washing rat-eye beans to provide washed rat-eye beans free from foreign materials and soaking the washed rat-eye beans in water for five hours;
   combining the soaked rat-eye beans in a steam pot along with rice straw, adding water to the soaked rat-eye beans and rice straw in an amount of ⅓ the volume of the rat eye-beans, and steaming the rat-eye beans and rice straw in weak flames for five hours to provide boiled water and steamed rat-eye beans;
   separating the steamed rat-eye beans from the boiled water and fermenting the boiled water in the steam pot at a temperature of 20 to 30° C. for two to three days to provide fermented water;

combining grapefruit juice with the fermented water in the steam pot at a weight ratio of 99:1 fermented water: grapefruit juice to provide a mixture, and heating the mixture in a closed state at a temperature of 110 to 120° C. for four to five hours to sterilize the mixture;
cooling the sterilized mixture at room temperature; and
packing the cooled, sterilized mixture in a volume of 50 to 100 milliliters using a pouch machine to provide the portable, rat-eye bean extract.

\* \* \* \* \*